United States Patent
Gaddy (12)

(10) Patent No.: US 6,340,581 B1
(45) Date of Patent: *Jan. 22, 2002

(54) BIOLOGICAL PRODUCTION OF PRODUCTS FROM WASTE GASES

(75) Inventor: James L. Gaddy, Fayetteville, AR (US)

(73) Assignee: Bioengineering Resources, Inc., Fayetteville, AR (US)

(*) Notice: Subject to any disclaimer, the term of this patent is extended or adjusted under 35 U.S.C. 154(b) by 0 days.

This patent is subject to a terminal disclaimer.

(21) Appl. No.: 09/219,395

(22) Filed: Dec. 23, 1998

Related U.S. Application Data

(60) Continuation-in-part of application No. 08/808,088, filed on Feb. 28, 1997, now Pat. No. 5,821,111, which is a continuation of application No. PCT/US96/11146, filed on Jul. 1, 1996, which is a continuation-in-part of application No. 08/674,417, filed on Jul. 1, 1996, now Pat. No. 5,136,577, which is a continuation-in-part of application No. 08/347,512, filed on Nov. 30, 1994, now Pat. No. 5,807,722, which is a continuation of application No. 08/258,446, filed on Jun. 10, 1994, now Pat. No. 5,593,886, which is a continuation of application No. 07/220,686, filed on Mar. 31, 1994, now abandoned, which is a division of application No. 07/968,857, filed on Oct. 30, 1992, now abandoned.

(51) Int. Cl.$^7$ ................ C12P 7/54; C12P 7/08
(52) U.S. Cl. ............. 435/140; 435/262.5; 435/266; 435/163
(58) Field of Search ............... 435/140, 161, 435/163, 135, 262.5, 266

(56) References Cited

U.S. PATENT DOCUMENTS

| | | | |
|---|---|---|---|
| 4,497,637 A | 2/1985 | Purdy et al. | 48/111 |
| 4,515,759 A | 5/1985 | Burnes et al. | 423/220 |
| 4,553,981 A | 11/1985 | Fuderer | 48/62 |
| 4,568,644 A | 2/1986 | Wang et al. | 435/161 |
| 4,652,526 A | 3/1987 | Hsu | 435/253 |
| 4,692,172 A | 9/1987 | Stellaccio et al. | 48/197 |
| 4,721,676 A | 1/1988 | Zeikus | 435/253 |
| 4,732,855 A | 3/1988 | Zeikus et al. | 435/141 |
| 4,771,001 A | 9/1988 | Bailey et al. | 435/139 |
| 4,919,813 A | 4/1990 | Weaver | 210/603 |
| 4,921,799 A | 5/1990 | Kitaura et al. | 435/167 |
| 4,935,360 A | 6/1990 | Klemps et al. | 435/140 |
| 4,994,093 A | 2/1991 | Wetzel et al. | 48/197 |
| 5,026,647 A | 6/1991 | Tomes et al. | 435/244 |
| 5,036,005 A | 7/1991 | Tedder | 435/161 |
| 5,059,288 A | 10/1991 | Curry | 203/43 |
| 5,077,508 A | 12/1991 | Sublette | 435/168 |
| 5,110,319 A | 5/1992 | Turpin et al. | 44/451 |
| 5,134,944 A | 8/1992 | Keller et al. | 110/234 |
| 5,173,429 A | 12/1992 | Gaddy | 435/163 |
| 5,238,469 A | 8/1993 | Briesacher et al. | 95/115 |
| 5,593,886 A | 1/1997 | Gaddy | |
| 5,807,722 A | 9/1998 | Gaddy | |
| 5,821,111 A | 10/1998 | Gaddy | |

FOREIGN PATENT DOCUMENTS

| | | |
|---|---|---|
| DE | 282750 A | 10/1987 |
| EP | 0282750 | 9/1988 |
| WO | WO 98/00558 | 1/1998 |

OTHER PUBLICATIONS

The Merck Index, 12th Editiion, items 7764, 1725, 1996.*

Gest, Howard and Kamen, Martin D., "Photoproduction of Molecular Hydrogen by *Rhodospirillum Rubrum*." (Jun. 3, 1949) Science, vol. 109, p. 558–559.

Bott, Michael and Thaurer, Rudolf K., "Proton Translocation Coupled to the Oxidation of Carbon Monoxide to $CO_2$ and $H_2$ in *Methanosarcina Barkeri*." (1989) p. 469–472.

Dashekvicz, M.P., Uffen, R.L., "Identification of a Carbon Monoxide–Metabolizing Bacterium as a Strain of *Rhodopseudomonas Gelatinosa* (Molish) van Niel." (Apr. 1979) International Journal of Systematic Bacteriology, p. 145–148.

Diekert, Gabriele and Ritter, Maria, "Carbon Monoxide Fixation into the Carboxyl Group of Acetate During Growth of *Agrobacterium Woodii* on $H_2$ and $CO_2$." (1983) FEBS Microbiology Letters 17, p. 299–302.

Fuller, R.C., "Photosynthetic Carbon Metabolism in the Green and Purple Bacteria." (1978) Chapter 36, p. 691–705.

Goar, B. Gene, "Sulfinol Process Has Several Key Advantages." (Jun. 30, 1969) The Oil and Gas Journal, p. 117–120.

Miller, Terry L. and Wolin, M.J., "Oxidation of Hydrogen and Reduction of Methanol to Methane is the Sole Energy Source for a Methanogen Isolated from Human Feces." (Feb. 1983) Journal of Bacteriology, p. 1051–1055.

O'Brien, Jill M., et al. "Association of Hydrogen Metabolism with Unitrophic or Mixotrophic Growth of *Mathanosarcina Barkeri* on Carbon Monoxide." (Apr. 1984) Journal of Bacteriology, p. 373–375.

Rensfelt, Erik, et al., "Fuel Gas from Municipal Waste in an Integrated Circulating Fluid–Bed Gasification/Gas–Cleaning Process." (1988).

(List continued on next page.)

Primary Examiner—Irene Marx
(74) Attorney, Agent, or Firm—Howson & Howson

(57) ABSTRACT

A method and apparatus are designed for converting waste gases from industrial processes such as oil refining, and carbon black, coke, ammonia, and methanol production, into useful products. The method includes introducing the waste gases into a bioreactor where they are fermented to various products, such as organic acids, alcohols, hydrogen, single cell protein, and salts of organic acids by anaerobic bacteria within the bioreactor. These valuable end products are then recovered, separated and purified.

20 Claims, 5 Drawing Sheets

OTHER PUBLICATIONS

Supperich, E. et al. "Carbon Monoxide Fixation into the Carboxyl Group of Acetyl Coenzyme A During Autotrophic Growth of Methanobacterium." (Feb. 1983) FEBS Letters, vol. 152, No. 1, p. 21–23.

Uffen, R.L., et al. "Mutants of *Rhodospirillum rubrum* Obtained After Long–Term Anaerobic Dark Growth." (Dec. 1971) Journal of Bacteriology, p. 1348–1356.

Uffen, Robert L., "Anaerobic Growth of a Rhodoseudomonas Species in the Dark With Carbon Monoxide as Sole Carbon and Energy Substrate." (Sep. 1976) Proc. Natl. Acad. Sci. USA, vol. 73, No. 9, p. 3298–3302.

Vignais, Paulette M., et al., "Hydrogenase, Nitrogenase, and Hydrogen Metabolism in the Photosynthetic Bacteria." (1985) Advances in Microbial Physiology, vol. 26, p. 155–234.

Demain, et al. "Industrial Microbiology and Biotechnology." (1986) AJM, p. 332–335.

Crueger and Crueger, "Biotechnology: A Textbook of Industrial Microbiology." $2^{nd}$ Ed., Sinauer Assoc., Inc., p. 74–89.

May, Patricia. "Biotechnology Company Set For Fayetteville." (Oct. 29, 1992) Springdale Morning News, p. 1A.

"Industrial Innovations For Tomorrow, New Process Uses Bacteria To Transform Waste Gases Into Useful Chemicals." (Aug. 1992) U.S. Dept. of Energy Publication.

Morinaga, Tsuyoshi and Kawada, Naoki. "The Production of Acetic Acid From Carbon Dioxiade and Hydrogen by an Anaerobic Bacterium." (1990) Journal of Biotechnology, 14, p. 187–194.

Barik, S., et al., "Biological Conversion of Coal Synthesis Gas to Methane." (Sep. 1987) Energy Progess, vol. 7, No. 3, p. 157–160.

Zeikus, J.G. "Chemical and Fuel Production by Anaerobic Bacteria." (1980) Annual Review Microbiology, p.423–464.

Alden, H., et al. "Energy from Biomass and Wastes." (Mar. 1991) IGT.

Bouvier, J.M., et al. "Gas–Solid Pyrolysis of Tire Wastes—Kinetics and Material Balances of Batch Pyrolysis of Used Types." (1987) Resources and Conservation, vol. 15, p. 205–214.

Maynowski, C.W., et al. "Fermentation as an Advantageous Route for the Production of an Acetate Salt for Roadway Deicing." (1985) American Chemical Society, vol. 24, p. 457–465.

Eds by Clayton, R.K. and Sistrom, W.R. "Photosynthetic Carbon Metabolism in the Green and Purple Bacteria, The Photosynthetic Bacteria." (1978) Plenum Press, New York, p. 691–705.

Tracey, C.A. and Ashare, E. "Biomethanation of Biomass Pyrolysis Gases." (Jun. 1981) Solar Energy Research Institute, p. 1–148.

Klasson, K. T., et al., "Bioconversion of Synthesis Gas into Liquid or Gaseous Fuels." (Aug. 1992) Enzyme Microbiology Technology, vol. 14, p. 602–608.

Klemps, R., et al. "Production of Acetic Acid by *Actogenium kivui*." (1987) Applied Microbiology and Technology, p. 229–234.

Waber, L.J. and Wood, H.G. "Mechanism of Acetate Synthesis from $CO_2$ by *Clostridium acidiurici*." (Nov. 1979) Journal of Bacteriology, vol. 140, p. 468–478.

Vignais, P.M., et al. "Hydrogenase, Nitrogenase, and Hydrogen Metabolism in the Photosynthetic Bacteria." (1985) Advances in Microbial Physiology, Vo. 26, p. 163–177.

Gest, H. and Kamen, M.D. "Photoproduction of Molecular Hydrogen by *Rhodopirillum rubrum*." (Jun. 3, 1949) Science, vol. 109, p. 558–559.

Kohimiller, E.F. Jr. and Gest, H. "Acids By *Rhodospirillum rubrum*." (Dec. 5, 1950) Dept. Of Microbiology, School of Medicine, Western Reserve University, Cleveland, Ohio, vol. 61, p. 269–282.

Diekert, G. and Ritter, M. "Carbon Monoxide Fixation into the Carboxyl Group of Acetate During Growth of *Acetobacterium woodii* on $H_2$ and $CO_2$." (1983) Federation of European Microbiological Societies, Microbiology Letters 17, p. 299–302.

Wiegel, Jurgen, et al. "Isolation from Soil and Properties of the Extreme Thermophile *Clostridium thermohydrosulfuricum*." (Sep. 1979) Journal of Bacteriology, p. 800–810.

Wardell, James M. and King, C. Judson. "Solvent Equilibra for Extraction of Carboxylic Acids from Water." (1978) Journal of Chemical and Engineering Data, vol. 23, No. 2, p. 144–148.

Helsel, R.W. "Removing Carboxylic Acids from Aqueous Wastes, CEP." (May 1977) Hydroscience Environmental Systems.

Leigh, J.A. et al. "*Acetogenium Kivui*, A New Thermophilic Hydrogen–Oxidizing, Acetogenic Bacterium." Arch. Microbiol. 129, 275–280.

Moller, et al. "Sporomusa, A New Genus of Gram–Negative Anaerobic Bacteria Including *Sporomusa Sphaeroides* Spec. Nov. And *Sporomusa Ovata* Spec. Nov." (1984) Arch Microbiology 139: 388–390.

Balch, et al. "Acetobacterium, A New Genus of Hydrogen–Oxidizing, Carbon Dioxide–Reducing, Anaerobic Bacteria." (Oct. 1977) Journal of Systematic Bacteriology, p. 355–361.

Lorowitz, William H. and Bryant, Marvin P. "*Peptostreptococcus Productus* Strain That grows Rapidly with CO as the Energy Source." (May 1984) Applied and Environmental Microbiology, p. 70–74.

Genther, B.R. Sharak and Bryant, M.P. "Growth of *Eubacterium Limosum* with Carbon Monoxide as the Energy Source." (Jan. 1982) Applied and Environmental Microbiology, p. 70–74.

Kerby, Lee Lynd R. and Zeikus, J.G. "Carbon Monooxide Metabolism of the Methylotrophic Acidogen *Butyribacterium Methylotrophicum*." (Jan. 1982) Journal of Bacteriology, p. 255–263.

Gottschalk, Gerhard and Braun Manfred. "Revival of Name *Clostridium Aceticum*." (Oct. 1981) International Journal of Systematic Bacteriology, p. 476.

Ohwaki, Kyoko and Hungate, R.E. "Hydrogen Utilization By Clostridia in Sewage Sludge." (Jun. 1977) Applied and Environmental Microbiology, p. 1270–1274.

Kerbv, R., et al. "Single–Carbon Catabolism in Acetogens: Analysis of Carbon Flow in *Acetobacterium woodii* and *Butyribacterium Methylotrophicum* by Fermentation and 13 C Nuclear Magnetic Resonance Measurement." (Sep. 1983) Journal of Bacteriology, p. 1208–1218.

Sugaya, K. et al. "Production of Acetic Acid by *Clostridium Thermoaceticum* in Batch and Continuous Fermentation." (1986) Biotechnology and Bioengineering, vol. XXVIII, p. 678–683.

Schwartz, Robert D. and Keller, Frederick A. Jr. "Isolation of a Strain of *Clostridium Thermoaceticum* Capable of Growth and Acetic Acid Production at pH 4.5." (Jan. 1982) Applied and Environmental Microbiology, p. 117–123.

Schwartz, Robert D. and Keller, Frederick A. Jr. "Acetic Acid Production By *Clostridium Thermoaceticum* in pH–Controlled Batch Fermentations at Acidic pH." (Jan. 1982) Applied and Environmental Microbiology, p. 1385–1392.

Daniel, Steven L., et al. "Characterization of the $H_2$– and CO–Dependent Chemolithotrophic Potentials of the Acetogens *Clostridium Thermoaceticum* and *Acetogenium Kivui*." (Aug. 1990) Journal of Bacteriology, p. 4464–4471.

Rothstein, David M. "*Clostridium Thermosaccarolyticum* Strain Deficient in Acetate Production." (Jan. 1986) Journal of Bacteriology, p. 319–320.

"Nickel Transport by the Thermophilic Acetogen *Acetogenium Kivui*." (May 1989) Applied and Environmental Microbiology, p. 1078–1081.

Yang, Hsuichin and Drake, Harold L. "Differential Effects of Sodium on Hydrogen– and Glucose– Dependent Growth of the Acetogenic Bacterium *Acetogenium Kivui*." Applied and Environmental Microbiology, p. 81–86.

Sanchez–Riera, F., et al. "Influence of Environmental Factors in the Production of R(–)–1,2–Propanediol by *Clostridium Thermosaccharolyticum*." Biotechnology Letters, vol. 9, No. 7, 449 et seq.

Bhatnagar, L. et al. "Analysis of Hydrogen Metabolism in *Methanosarcina Barkeri:* Regulation of Hydrogenase and Role of CO–Dehydrogenase in $H_2$ Production." (1987) Federation of European and Microbiological Societies, Microbiology Letters 41, p. 337–343.

Dashekvicz, M.P. and Uffen, R.L. "Identification of a Carbon Monoxide–Metabolizing Bacterium as a Strain of *Rhodoseudomonas Gelantinosa* (Molish) Van Niel." (Apr. 1979) International Journal of Systematic Bacteriology, vol. 29, p. 145–148.

Uffen, R.L., et al. "Mutants of *Rhodospirillum Rubrum* Obtained After Long–Term Anaerobic, Dark Growth." (Dec. 1973) Journal of Bacteriology, vol. 108, No. 3, p.1348–1356.

Thauer, R.K. et al. "The Active Species on CO2 Utilized By Reduced Ferredoxin: $CO_2$ Oxidoreductase from *Clostridium Pasteurianum*." (1975) European Journal of Biochemistry, 55, 111–117.

Barik, S., et al. "Biological Production of Alcohols from Coal Through Indirect Liquefaction." (1988) The Humana Press, p. 363–378.

Klasson, K.T., et al. "Biological Production of Liquid and Gaseous Fuels from Synthesis Gas." (1990) Applied Biochemistry and Biotechnology, vol. 24/25.

Vega, J.L., et al. "The Biological Production of Ethanol from Synthesis Gas." (1989) Applied Biochemistry and Biotechnology, vol. 20/21.

Martin, D.R. et al. "Carbon Monoxide–Dependent Evolution of Hydrogen by the Homoacetate–Fermenting Bacterium *Clostridium Thermoaceticum*." (1983) Current Microbiology, vol. 8, p. 337–340.

O'Brien, J.M., et al. "Association of Hydrogen Metabolism with Unitrophic or Mixotrophic Growth of *Methanosarcina Barkeri* on Carbon Monoxide." (Apr. 1984) Journal of Bacteriology, vol. 158, No. 1, p. 373–375.

Uffen, R.L. "Anaerobic Growth of a Rhodopseudomonas Species in the Dark with Carbon Monoxide as Sole Carbon and Energy Substrate." (Sep. 1976) Microbiology, vol. 73, No. 9, p. 3298–3302.

Goar, B.G. "Sulfinol Process has Several Key Advantages." (Jun. 30, 1969) The Oil and Gas Journal, p. 117–120.

Stupporich, E., et al. "Carbon Monoxide Fixation into the Carboxyl Group of Acetyl Coenzyme A During Autotrophic Growth of Methanobacterium." (Feb. 1983) Federation of European Biochemical Societies, Microbiology Letters, vol. 152, No. 1, p. 21–23.

Bott, M. and Thauer, R.K. "Proton Translocation Coupled to the Oxidation of Carbon Monoxide to $CO_2$, and $H_2$ in *Methanosarcina Barkeri*." (1989) European Journal of Biochemistry, p. 469–472.

Anderson, L. and Fuller, R.C. "Photosynthesis in *Rhodospirillum Rubrum* I. Autotrophic Carbon Dioxide Fixation." (1967) Plant Physiology, p. 487–490.

Barik, S., et al. "Biological Upgrading of Coal–Derived Synthesis Gas: Final Report (Abstract)." (1989) Fossil Fuels, vol. 110, p. 201.

Kawakami, S., et al. "Pyrolysis Process for Scrap Tires." (1980) American Chemical Society Symposium Series, 130, Washington, D.C.

Rensfelt, E. and Ekstrom, C. "Biomass and Wastes." (1991)Inst. Gas Tech.

Zeikus, J.G. "Chemical and Fuel Production by Anaerobic Bacteria." (1980) Annual Review of Microbiology, p. 423–464.

Lundback, K.M.O., et al. "Parameters Affecting the Kinetics of Ethanol Production from CO, $CO_2$, and $H_2$ by *clostridium ljungdahlii*." (May 1990) Presented at Twelfth Symposium on Biotechnology for Fuels and Chemicals, Gatlinsburg, Tennesse.

Tanner, R.S. and Yang, D. "*Clostridium ljungdahlii* PETC Sp. Nov. A New Acetogenic, Gram–Positive, Anaerobic Bacterium." (1990) Abstracts of the 1990 Annual Meeting of the American Society for Microbiology, No. R–21, p. 249.

Gaddy. "Indirect Coal Liquification." (1985) Technical Report.

Vega, J.L. et al. "Study of Gaseous Substrate Fermentations: Carbon Monoxide Conversion to Acetate. 2. Continuous Culture." (Sep. 1989) Biotechnology and Bioengineering, vol. 34, p. 785–793.

Nakamura, et al. "Taxonomic Study of *Bacillus Coagulans* Hammer 1915 with a Proposal for *Bacillus Smithii* sp. Nov." (Jan. 1988) International Journal of Systematic Bacteriology, vol. 38, p. 63–73.

Krueger, et al. "Thermophilic Bacilli Growing with Carbon Monoxide." (Nov. 1984) Archives of Microbiology. vol. 139, No. 4, p. 402–408.

Arora, D., et al. "Production of Ethanol from Refinery Waste Gases, Phase II—Technology Development." (Jul., 1985) Annual Report, in Energy Conservation, p. 1–56.

Arora, D., et al. "Production of Ethanol from Refinery Waste Gases, Phase III—Engineering Development." (Nov. 1996) Annual Report, in Energy Conservation, p. 1–23.

Arora, D., et al. "Production of Ethanol from Refinery Waste Gases, Phase,", (Aug. 1997) Final Report, in Energy Conservation, pp. 1–96.

DOE Report, "High Pressure Synthesis Gas Conversion: Task 3: High Pressure Profiles," DOE/PC/91028–T6; Order No. DE93040517, 53 pages Available: NTIS from: Energy Research Abstracts, 18(11), Abstract No. 32677 (1993).

Chemical Abstracts, 123(1), Columbus, Ohio, Abstract No. 7982, Jul. 3, 1995, "High Pressure Synthesis Gas Conversion: Task 3: High Pressure Profiles," XP002117033.

DOE Report, "Biological Production of Ethanol from Coal: Tasks 4 Report, Continuous Reactor Studies," DOE/PC/89876–T17; Order No. DE93009047, 176 pages Available: NTIS from: Energy Research Abstracts, 18(5), Abstract No. 11669 (1993).

Chemical Abstracts, 120(22), Columbus, Ohio, Abstract No. 275289, May 30, 1994, "Biological Production of Ethanol from Coal: Task 4 Report, Continuous Reactor Studies," XP002117034.

DOE Report, "High Pressure Synthesis Gas Fermentation," DOE/PC/91028–T5; Order No. DE92019656, 21 pages Available: NTIS from: Energy Research Abstracts, 17(12), Abstract No. 33274 (1992).

Chemical Abstracts, 119(7), Columbus, Ohio, Abstract No. 269118, Dec. 20, 1993, "High Pressure Synthesis Gas Fermentation," XP002117035.

R.S. Tanner et al., "*Clostridium ljungdahlii* sp. nov., an Acetogenic Species in Clostridial rRNA Homology Group I," *Int. J. Syst. Bacteriol.*, 43(2): 232–236 (Apr. 1993).

K. T. Klasson et al., "Bioliquefaction of Coal Synthesis Gas," *Am. Chem. Soc., Div. Fuel Chem.*, 37(4): 1977–1982 (1992).

B. B. Elmore, "Biological Production of Ethanol from Coal Synthesis Gas using *Clostridium Ljungdahlii*, Strain PETC", Univ. Microfilms Int., Order No,. DA9111206 from: Diss. Abstr. Int. B 1991, 51(11), 5459 (1990).

Chemical Abstracts, 115(9), Columbus, Ohio, Abstract No. 90621, Sep. 2, 1991, XP002117038: B. B. Elmore, "Biological Production of Ethanol from Coal Synthesis Gas using *Clostridium ljungdahlii*, Strain PETC".

* cited by examiner

BIOLOGICAL PRODUCTION OF PRODUCTS FROM WASTE GASES

This is a continuation of International Patent Application No. PCT/US96/11146, filed Jul. 1, 1996, and a continuation-in-part of U.S. patent application Ser. No. 08/674,417, filed Jul. 1, 1996, now U.S. Pat. No. 6,136,577 which is a continuation-in-part of U.S. patent application Ser. No. 08/347,512, filed Nov. 30, 1994, issued as U.S. Pat. No. 5,807,722, which is a continuation application of U.S. patent application Ser. No. 08/258,446, filed Jun. 10, 1994, issued as U.S. Pat. No. 5,593,886, which is a divisional application of U.S. patent application Ser. No. 07/968,857, filed Oct. 30, 1992, now abandoned. This application is also a continuation-in-part of U.S. patent application Ser. No. 08/808,088, filed Feb. 28, 1997, issued as U.S. Pat. No. 5,821,111, which is a continuation of U.S. patent application Ser. No. 07/220,686, filed Mar. 31, 1994, now abandoned.

This invention was supported by the U.S. Department of Energy, Grant Nos. DE-FCO2-90CE40939 and DE-FC04-94AL98770. The U.S. Government has certain rights in this invention.

FIELD OF THE INVENTION

The present invention is directed to biologic methods, processes, microorganisms, and apparatus for producing products, materials, intermediates, and the like such as organic acids, single cell protein ("SCP"), hydrogen, alcohols, and organic acid salts from the waste gas streams of certain industrial processes and more particularly concerns a process utilizing continuous gaseous substrate fermentation under anaerobic conditions to accomplish this conversion.

BACKGROUND OF THE INVENTION

The conventional procedure for producing organic acids, alcohols, hydrogen and organic acid salts is chemical synthesis of petroleum-derived feedstocks. The rapidly escalating cost of petroleum has generated considerable interest in producing these valuable commodities by fermentative processes that utilize renewable or waste materials as the feedstock. Single cell protein is produced as a by-product of the fermentations, and is generally used as an animal feed supplement.

There is also growing concern over the massive amounts of atmospheric pollutants and greenhouse gases produced by conventional industrial processes. The Environmental Protection Agency recently estimated that over six million metric tons of carbon monoxide and nearly four million metric tons of hydrogen were discharged annually by the industrial complex. A substantial portion of this waste carbon monoxide and hydrogen is the result of carbon black manufacture and coke production, roughly 2.6 million metric tons of carbon monoxide and 0.5 million metric tons of hydrogen. Large amounts of carbon monoxide or hydrogen are also produced by the ammonia industry (125,144 metric tons of carbon monoxide in 1991), petroleum refining (8 metric tons per thousand barrels), steel mills (152 pounds per metric ton of steel produced), and sulfate pulping of wood (286 pounds per ton of pulp). In 1991, the adipic acid industry generated 40,773 metric tons of carbon monoxide that was burned for fuel value or flared. In many cases, these gases are discharged directly to the atmosphere, placing a heavy pollution burden on the environment.

Typically, the waste gases from the manufacture of industrial products are released at low pressures and temperatures. Current technology cannot utilize these dilute gases under such conditions. Adapting existing technology to separate and recover hydrogen or carbon monoxide from these waste streams would be expensive and impractical.

In light of the foregoing, there exist needs in the art for cost effective and practical methods, microorganisms, and apparatus for utilizing the above-described waste gases and for producing products, materials, intermediates and the like such as organic acids, alcohols, hydrogen and organic acid salts by other than chemical synthesis of petroleum derived feedstocks.

SUMMARY OF THE INVENTION

In accordance with the present invention, products, materials, intermediates, and the like such as organic acids, alcohols, hydrogen, single cell protein and/or organic acid salts are produced from the waste carbon monoxide, hydrogen, and/or carbon dioxide of industrial processes, thereby reducing environmental pollution while at the same time saving energy and chemical feedstocks.

In accordance with an exemplary process of the present invention, the desired components of the dilute gas mixtures are introduced into a bioreactor containing one or more cultured strains of anaerobic bacteria that utilize the waste gas components by a direct pathway to produce a desired compound. The compound is recovered from the aqueous phase in a separate vessel or vessels, utilizing a suitable recovery process for the compound produced. Examples of recovery processes include extraction, distillation or combinations thereof, or other efficient recovery processes. The bacteria are removed from the aqueous phase and recycled to avoid toxicity and maintain high cell concentrations, thus maximizing reaction rates. Cell separation, if desired, is accomplished by centrifugation, membranous ultrafiltration, or other techniques.

The principal object of the present invention is the provision of a process and/or microorganism for the production of products, intermediates, materials, and the like such as organic acids, hydrogen, single cell protein, alcohols, and/or organic acid salts from carbon monoxide, hydrogen, and/or carbon dioxide.

Another object of the present invention is the provision of methods, microorganisms and apparatus for the production of items such as organic acids, alcohols, hydrogen, single cell protein and/or salts from the waste gas streams of industrial processes such as oil refining, and production methods for generating carbon black, coke, ammonia, and methanol.

A still further object of the present invention is the provision of a process for producing acetic acid and/or ethanol from a waste gas stream of identical composition to that found in the manufacture of carbon black.

Yet another and more particular object of the present invention is the provision of a method, microorganism and apparatus involving continuous gaseous substrate fermentation under anaerobic conditions to accomplish the conversion of waste gas streams of certain industrial processes into useful products such as organic acids including acetic acid, alcohols, hydrogen, single cell protein and organic acid salts.

Other objects and further scope of the applicability of the present invention will become apparent from the detailed description to follow, taken in conjunction with the accompanying drawings wherein like parts are designated by like reference numerals.

DETAILED DESCRIPTION OF THE INVENTION

Figure 1:
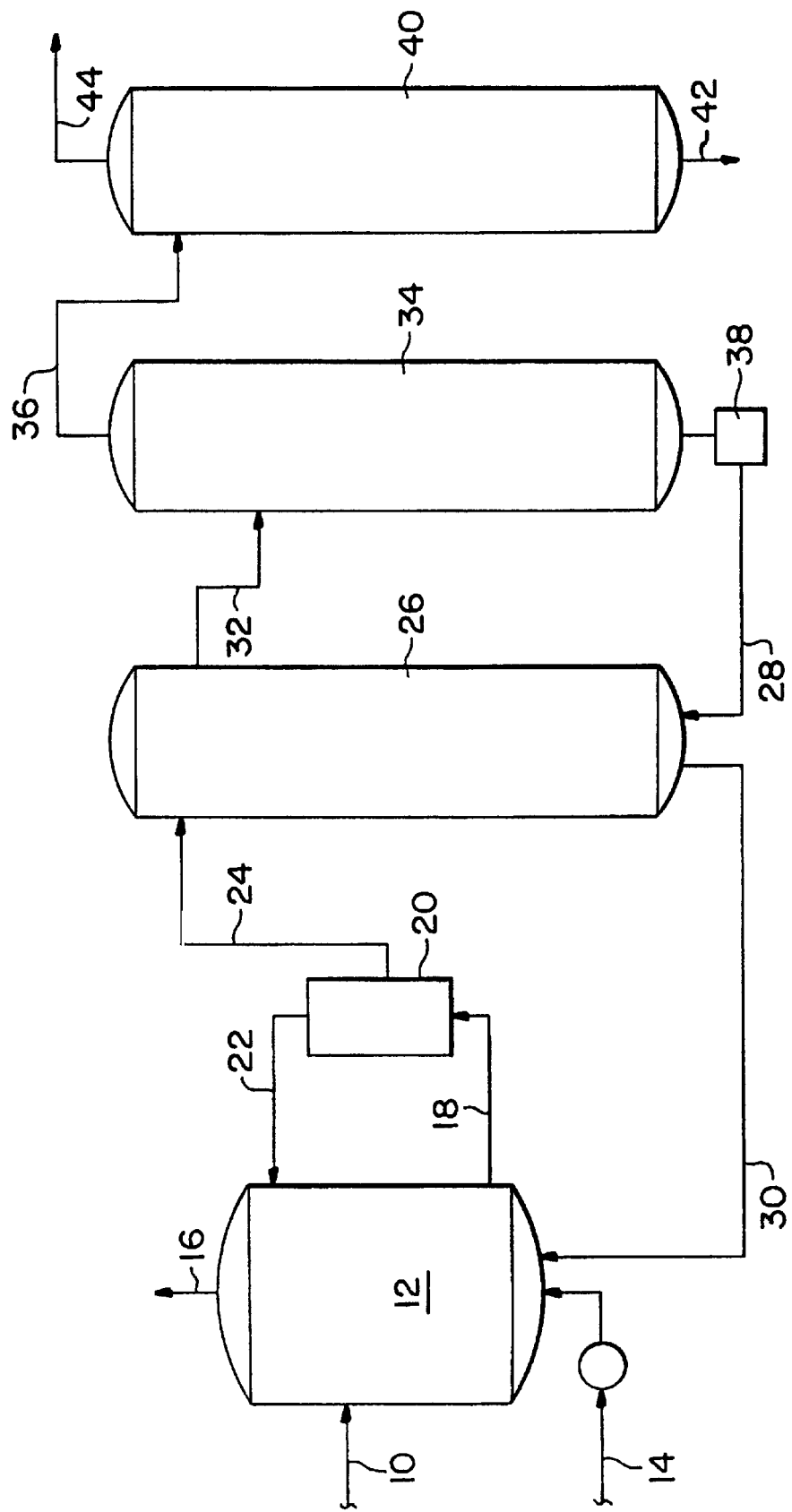
FIG. 1 is a schematic diagram of a process of this invention for the production of acetic acid from waste gas.

The term "waste gas" or "waste gas streams" as used herein means carbon monoxide and hydrogen mixed with other elements or compounds, including carbon dioxide, nitrogen and methane, in a gaseous state, which gases or streams are typically released or exhausted to the atmosphere either directly or through combustion. Normally, release takes place under standard smokestack temperatures and pressures. Accordingly, the processes of the present invention are suitable for converting these atmospheric pollutants into useful products such as organic acids, alcohols and organic acid salts. These products include, but are not limited to acetic, propionic, and butyric acids; methanol, ethanol, propanol, and n-butanol; plus salts, such as calcium magnesium acetate (CMA) and potassium acetate (KA).

Anaerobic bacteria which are know to convert carbon monoxide and water or hydrogen and carbon dioxide into alcohols and acids and acid salts include *Acetobacterium kivui, A. woodii, Clostridium aceticum, Butyribacterium, methylotrophicum, C. acetobutylicum, C. formoaceticum, C. kluyveri, C. thermoaceticum, C. thermocellum, C. thermohydrosulfuricum, C. thermosaccharolyticum, Eubacterium limosum, C. ljungdahlii* PETC and *Peptostreptococcus productus.* Anaerobic bacteria known to produce hydrogen from carbon monoxide and water include *Rhodospirillum rubrum* and *Rhodopseudomonas gelatinosa.*

More specifically, bacterial species such as *Acetogenium kivui, Peptostreptococcus productus, Acetobacterium woodii, Clostridium thermoaceticum* and *Eubacterium limosum,* produce acetate by the reaction:

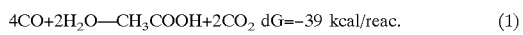
$$4CO + 2H_2O \longrightarrow CH_3COOH + 2CO_2 \quad dG = -39 \text{ kcal/reac.} \quad (1)$$

Many anaerobic bacteria are also known to produce acetic acid from hydrogen and carbon dioxide. These bacterial isolates include *A. kivui, P. productus,* and *Acetobacterium sp.,* which utilize homoacetic fermentation by anaerobically oxidizing hydrogen and carbon dioxide according to the equation:

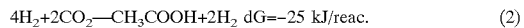
$$4H_2 + 2CO_2 \longrightarrow CH_3COOH + 2H_2O \quad dG = -25 \text{ kJ/reac.} \quad (2)$$

*Acetobacterium woodii* and *Acetoanaerobium noterae* produce acetate from hydrogen and carbon dioxide according to the above reaction, but in addition to acetate, *A. noterae* produces some propionate and butyrate. Another chemolithotrophic bacterium, *Clostridium aceticum,* produces acetate from carbon dioxide using a glycine decarboxylase pathway.

Some bacteria, like *A. kivui, P. productus,* and *A. woodii,* produce acetate from either carbon monoxide and water, or hydrogen and carbon dioxide. *P. productus* gives particularly fast rates of conversion and demonstrates high tolerance to carbon monoxide; however, this organism shows a preference to follow Equation (1) over Equation (2).

In addition to these listed bacteria, two strains of an additional clostridia which produce acetic acid or ethanol from carbon monoxide and water, or hydrogen and carbon dioxide have been isolated. One is *Clostridium ljungdahlii* ERI2, a rod-shaped, gram positive, non-thermophilic anaerobe which gives superior acetic acid yields and operates at a low pH, a characteristic which greatly enhances the recovery of the product. *C. ljungdahlii* ERI2 carries out a vigorous acetogenic fermentation of glucose. It also infrequently forms spores and carries out a primarily acetogenic fermentation of hexose or $H_2:CO_2$. It is motile with peritrichous flagellation. This new strain of *C. ljungdahlii,* referred to as ERI2, was isolated from a natural water source and was deposited with The American Type Culture Collection, 10801 University Boulevard, Manassas, Va. on Dec. 8, 1992, under Accession No. 55380. The deposit was made freely available to the public on Nov. 6, 1997.

In preparing the products of the present invention, "mixed strains" of the bacteria enumerated hereinabove may be utilized. By mixed strains, it is meant a mixed culture of two or more anaerobic bacteria. This mixed strain, when utilized in the process described herein, produces organic acids (such as acetic acid and the like) or salts thereof, alcohols, hydrogen, single cell protein, etc.

In the development of the present invention, new strains of anaerobic bacteria have been isolated which enact this conversion with high efficiency. In addition, modifications to the fermentation conditions can result in the production of ethanol instead of acetic acid in some strains. Depending on the specific microorganism(s) utilized, variables which must be considered in forming products from waste gases include nutrient constituents and concentrations, medium, pressure, temperature, gas flow rate, liquid flow rate, reaction pH, agitation rate (if utilizing a Continuously Stirred Tank Reactor), inoculum level, maximum substrate (introduced gas) concentrations to avoid inhibition, and maximum product concentrations to avoid inhibition.

In accordance with an exemplary embodiment of the present invention and as shown in FIG. 1, a first step in the conversion process is the preparation of nutrient media (10)

for the anaerobic bacteria. The content of the nutrient media will vary based on the type of anaerobe utilized and the desired product. The nutrients are constantly fed to a bioreactor or fermenter (12), consisting of one or more vessels and/or towers of a type which includes the Continuously Stirred Reactor (CSTR), Immobilized Cell Reactor (ICR), Trickle Bed Reactor (TBR), Bubble column, Gas Lift Fermenters, or other suitable fermentation reactor. Within the bioreactor (12) resides the culture, either single or mixed species, of anaerobic bacteria utilized in the gas conversion process. For the CSTRs, TBRs, Bubble Columns and Gas Lift Fermenters, these bacteria live dispersed throughout the liquid phase of the reactor, but for ICRs, the bacteria adhere to an internal packing medium. This packing medium must provide maximal surface area, high mass transfer rate, low pressure drop, even gas and liquid distribution, and must minimize plugging, fouling, nesting and wall channeling. Examples of such medium materials are ceramic Berl saddles, Raschig rings or other high performance packings.

The waste gases (14) are continuously introduced into the bioreactor (12). The gas is retained in the bioreactor (12) for the period of time which maximizes efficiency of the process. Exhaust gases (16), containing inert substances and unreacted substrate gases, are then released. The liquid effluent (18) is passed to a centrifuge, hollow fiber membrane, or other filtration device (20) to separate out microorganisms that are entrained. These microorganisms (22) are returned to the bioreactor (12) to maintain a high cell concentration which yields a faster reaction rate (cell recycle).

A next step in the process is separation of the desired biologically produced product(s) from the permeate or centrifugate (24). In the embodiment depicted in FIG. 1, the permeate or centrifugate (24) is passed to an extraction chamber (26) where it is contacted with a solvent (28). The solvent (28) should have a high distribution coefficient for the desired end product, a high recovery factor, low toxicity to humans, low toxicity to the bacteria, immiscibility with water, an appropriately high boiling point, and should form no emulsion with the bioreactor constituents. The distribution of solute between solvent and aqueous phases will determine the thermodynamic feasibility and the amount of solvent required to remove the end product. Typical solvents include secondary and tertiary amines in a suitable solvent, tributyl phosphate, ethyl acetate, tri-octyl phosphine oxide and related compounds in a suitable co-solvent, long chain alcohols, hexane, cyclohexane, chloroform, and tetrachloroethylene.

The nutrients and materials in the aqueous phase (30) pass back to the bioreactor (12) and the solvent/acid/water solution (32) passes to a distillation column (34), where it is heated to a sufficient temperature to separate the solvent (28) from the acid and water (36). The solvent (28) passes from the distillation column (34) through a cooling chamber (38) to lower the temperature to the optimum temperature for extraction, then back to the extraction chamber (26) for reuse. The acid and water solution (36) passes to a final distillation column (40) where the desired end product (42) is separated from the water and removed. The water (44) is recirculated for nutrient preparation.

Figure 2:
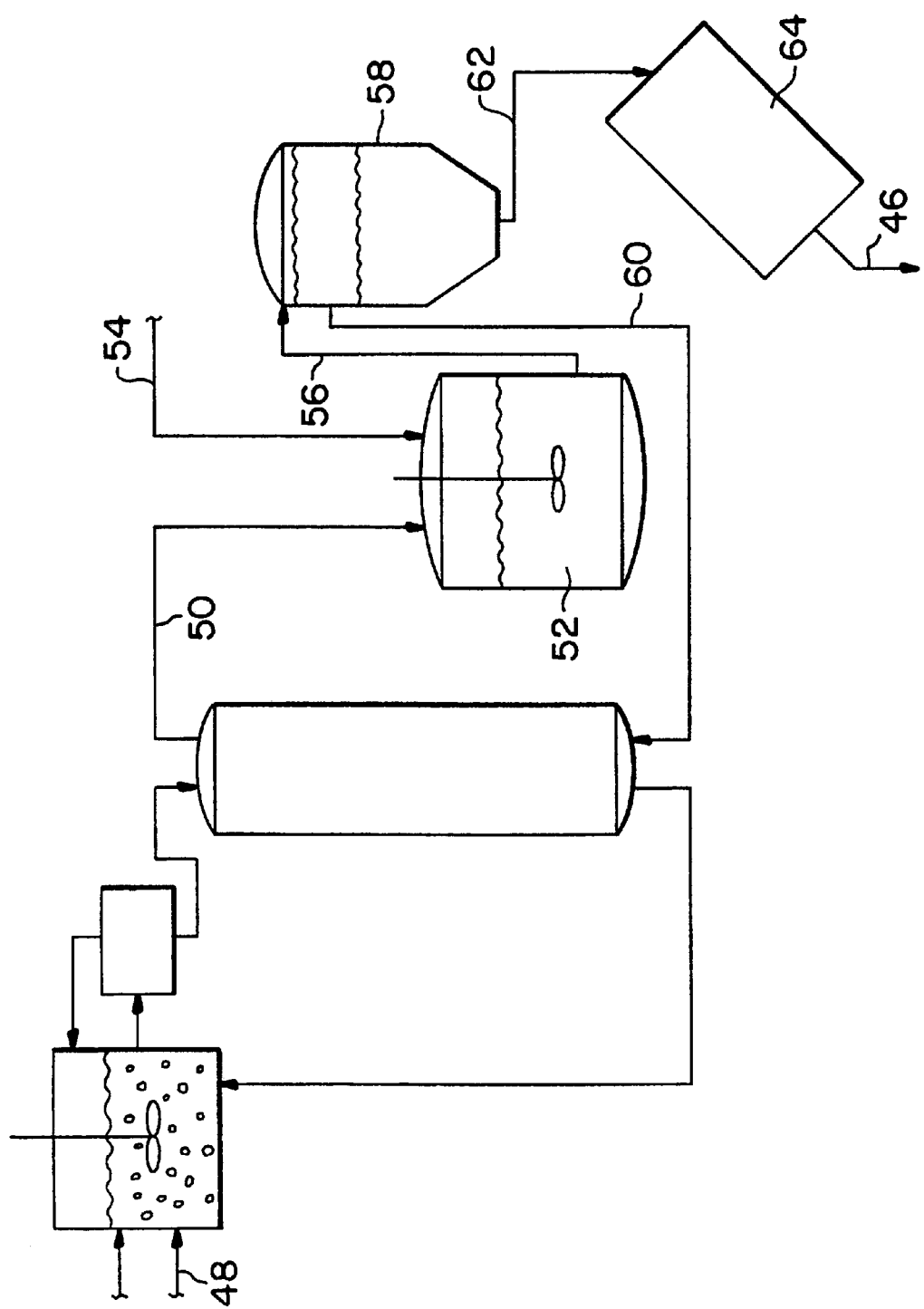
FIG. 2 is a schematic diagram of a process of this invention for the production of calcium magnesium acetate salt (CMA) from waste gas.

FIG. 2 shows a process for the production of the road deicer, calcium magnesium acetate (CMA) (46), from waste gas (48). The process is identical to the acetic acid process of FIG. 1 through solvent extraction. Identical organisms, nutrients and process conditions are used in continuous fermentation, including the reaction vessels. Similarly, cell recycle by hollow fiber membrane, centrifugation or other filtration devices are identically employed in this process. Finally, the extraction of acetic acid in an extraction chamber, followed by recycle of the acid-free medium, is employed.

After extraction, the process for producing CMA differs greatly from the acetic acid production process of FIG. 1. In the CMA process the solvent (50) containing acetic acid and a small amount of water is sent to a reaction vessel (52) for CMA production. The water content of the solvent stream is dependent upon the solvent used for acetic acid extraction. Again, solvents such as secondary and tertiary amines in a suitable co-solvent, tributyl phosphate, ethyl acetate, tri-octyl phosphine oxide and related compounds in a suitable co-solvent, long chain alcohols, hexane, cyclohexane, chloroform and tetrachloroethylene may be employed with varying success. The reaction vessel (52) for CMA is most suitably a Continuous Stirred Tank Reactor (CSTR), although other reactor systems may be employed. A mixture (54) of dolomitic lime and magnesium oxide in water is added to the solvent containing acetic acid and water. Reaction occurs to produce CMA in aqueous solution at or below the saturation level.

The CMA, water and solvent (56) are then sent to a settling device (58) to separate the aqueous and solvent phases. The solvent phase (60) is returned to the extraction chamber for recycle. The CMA/water (62) is sent to drying/pelletizing means (64) to produce a pelletized CMA product.

Potassium acetate (KA) can be produced as an alternative product by substituting caustic potash (or potassium oxide) for the dolomitic lime. Since KA is produced as a 50 percent aqueous solution, drying and pelletizing are not required.

Figure 3:
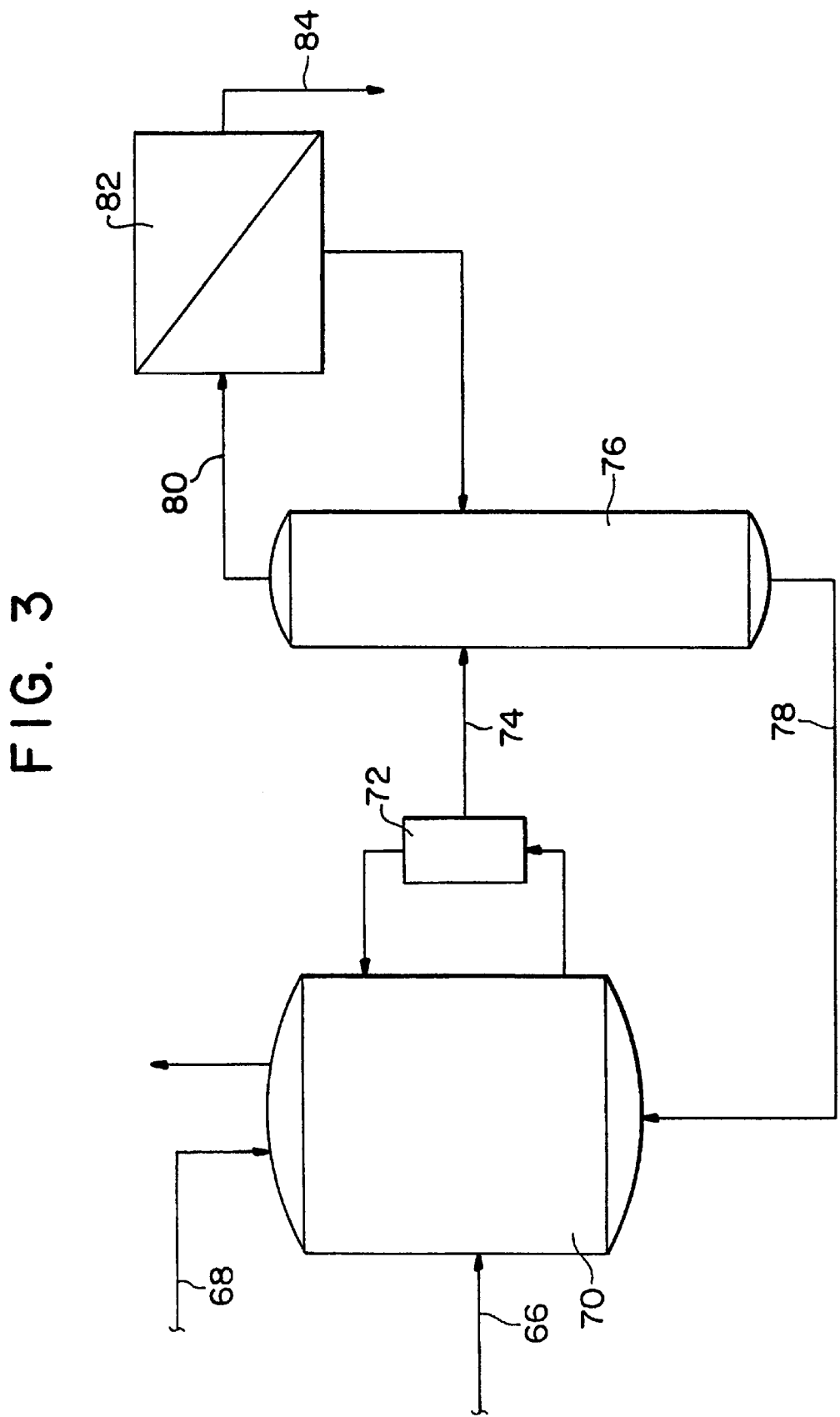
FIG. 3 is a schematic diagram of a process of this invention for the production of ethanol from waste gas.

FIG. 3 shows a process of this invention for the production of ethanol from waste gas. As in FIG. 1, water gas (66) and nutrients (68) are fed into a reactor (70) containing a culture of microorganisms. The reactor may be any of the types described above in the narrative of FIG. 1. The organism used in the ethanol production process must be capable of producing ethanol in place of acetic acid/acetate. In general, a low fermentation pH of 4.0–5.5 is required, coupled with a nutrient limitation. The bacteria listed hereinabove which are capable of operating at these reduced pH levels can be used in this process of ethanol production.

Waste gas is fed into the reactor containing the culture of organisms capable of ethanol production along with the required nutrients. Ethanol is produced as the product in a similar fashion as in FIG. 1. Cell recycle (72) may be used to enhance the cell concentration in the reactor, but this operation is not required to make the process work. The permeate (74) from the cell recycle apparatus containing dilute ethanol in medium is sent to distillation (76), where the water (78) and ethanol (80) are separated. Ninety-five percent ethanol exits the top of the distillation column and water (spent medium) exits the bottom of the column. The spent medium is sent back to the reactor as water recycle. The 95 percent ethanol is sent to a molecular sieve system (82) to produce anhydrous ethanol (84).

Thus in accordance with the present invention, it is now possible to produce valuable organic acids, alcohols, or organic acid salts by a gaseous substrate fermentation, not only reducing consumption of valuable chemical feedstocks, but also removing hazardous atmospheric pollutants from the waste gas streams of many industries. Previous processes to derive these chemicals biologically were based on fermentation of sugars.

In the processes described hereinabove, it is preferred that the process is conducted at higher than 1 atmosphere. Preferably, it is preferred that it be conducted at pressures up to 320 atmospheres, and more preferably up to 20 atmospheres, and most preferably up to 15 atmospheres.

The following specific examples are submitted to illustrate but not to limit the present invention. Unless otherwise indicated, all parts and percentages in the specification and claims are based upon volume.

EXAMPLE 1
Production of Acetic Acid from Carbon Black Waste Gases

This example is directed to a process utilized to convert waste gas of a composition which matches that of the furnace exhaust of carbon black manufacture to acetic acid. The waste gas has a composition of about 13 percent carbon monoxide, 14 percent hydrogen, and 5 percent carbon dioxide, with the remaining 68 percent largely nitrogen, with traces of oxygen and sulfur compounds. The waste gases are produced as the result of partial oxidation of gas or oil with insufficient air to form amorphous carbon, with about 1.2 pounds of carbon monoxide produced per pound of elemental carbon. These waste gases form a serious atmospheric contamination problem and also represent a valuable chemical feedstock resource not presently being recovered.

In the development of the present process, two distinct routes to produce acetic acid from carbon black waste gases were studied. The direct route converts carbon monoxide and water, or hydrogen and carbon dioxide, directly into acetic acid according to Equations (1) and (2), respectively. An indirect route involves the conversion of carbon monoxide and water into hydrogen and carbon dioxide by the water gas shift reaction, followed by production of acetic acid from hydrogen and carbon dioxide. This indirect route was found to be a less efficient utilization of the technology. The acetogens tested are summarized in Table 1.

TABLE 1

Acetogenic Bacteria Tested for CO, $H_2$, and $CO_2$ Conversion

| Bacterial Route | Simultaneous Consumption of CO and $H_2$ |
|---|---|
| Direct Route | |
| P. productus | No |
| E. limosum | No |
| A. noterae | No |
| C. aceticum | No |
| C. thermoaceticum | No |

TABLE 1-continued

Acetogenic Bacteria Tested for CO, $H_2$, and $CO_2$ Conversion

| Bacterial Route | Simultaneous Consumption of CO and $H_2$ |
|---|---|
| S. sphaeroides | No |
| A. woodii | Yes |
| A. kivui | Yes |
| C. ljungdahlii ERI2 | Yes |
| Indirect Route | |
| R. gelatinosa | No |
| R. rubrum | No |

Among these bacteria that produce acetic acid directly from carbon monoxide, A. kivui and the newly isolated strain, C. ljungdahlii ERI2, show far superior rates for both carbon monoxide and hydrogen utilization. Further experimentation proceeded using these two anaerobic bacteria. There are obvious advantages to the use of bacteria that can utilize carbon monoxide and hydrogen simultaneously. Such use would afford the most efficient use of the waste gases and remove the greatest amount of atmospheric pollutants.

A. Bench Scale Operation of the Described Process to Produce Acetic Acid

Figure 4:
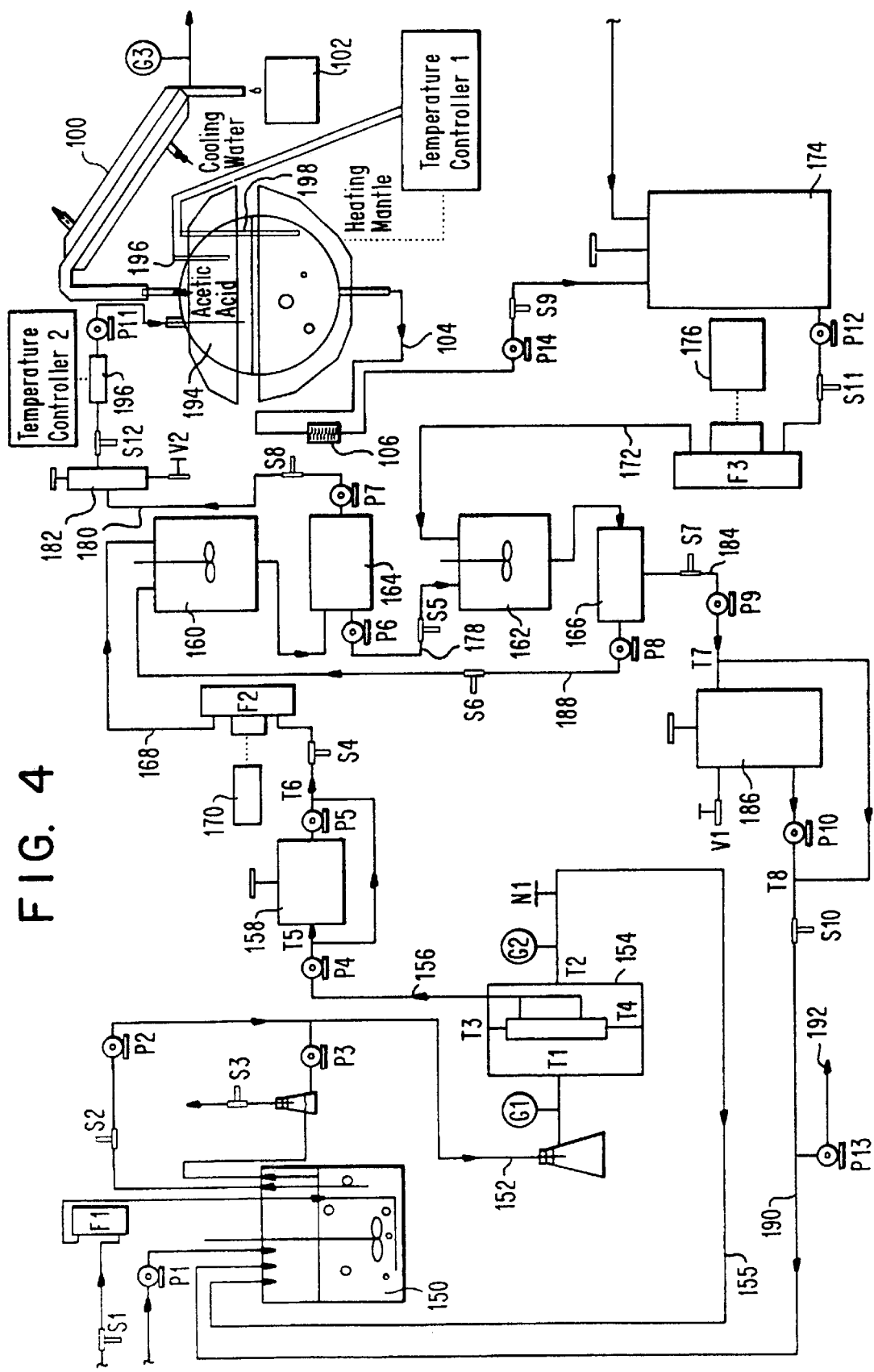
FIG. 4 is a schematic representation of a continuous fermentation system in accordance with an embodiment of the present invention.

As shown in FIG. 4 and in accordance with one embodiment of the present invention, a bench scale continuous conversion system is shown to include a BioFlo IIC fermentor (150) [New Brunswick Scientific Co., Inc., Edison, N.J.]. The fermentor (150) is equipped with an agitation motor, pH controller, foam controller, thermostat, dissolved oxygen probe, nutrient pump, and 2.5 L culture vessel. The working volume is variable (1.5–2.0 L). Other variable operational parameters include medium feeding rate (Dilution rate), gas flow rate (Gas retention time), and agitation (rpm). The vented or exhaust gases exit the fermentor (150) through a condenser fixed to a vented hood via a water trap and a sampling port.

The culture broth (152) is recycled through a cross-flow hollow fiber module (154) by a peristaltic pump [Cole Parmer]. The recycling rate is about 80–100 mL/minute. The hollow fiber module (154) has the following characteristics: the surface area is 0.35 $ft^2$, the pore size is 0.2 $\mu$m and the lumen diameter is 1 mm. The permeate (156) is pumped to a storage tank (158) (Feed storage). The culture cells are returned to the fermenter along line (155).

A countercurrent acetic acid extraction system, including two stage mixer and settler components includes first and second mixers (160) and (162) and first and second settling tanks (164) and (166). The permeate (168) from storage (158) is pumped to mixer (160) through a flow controller (170). The solvent (172) is pumped to mixer (162) from solvent storage (174) through a flow controller (176). Both mixer (160) and mixer (162) are equipped with stirring mechanisms to achieve good mixing of aqueous phase and solvent phase. The mixture of both phases from the mixers (160) and (162) is led to settlers (164) and (166), respectively. The phase separation is accomplished in the settlers. The aqueous phase (178) from settler (164) is pumped to mixer (162); the solvent phase (180) from settler (164) is pumped to a separator (182); the aqueous phase (184) from settler (166) is pumped to raffinate storage (186); and the solvent phase (188) from settler (166) is pumped to mixer (160). The raffinate is recycled to the CSTR 50 along a line (190). This recycle line (190) is partially bled at (192) to remove inhibiting factors.

The solvent (180) loaded with acetic acid is pumped to a distillation flask (194) through a preheater (196). The distillation flask (194) is equipped with two thermocouples (196) and (198) to monitor and control temperature in the liquid phase and gas phase. The heating temperature for distillation is set to achieve maximum vaporization of the acetic acid. The acetic acid vapors are condensed in a condenser (100) and collected in a flask (102). The stripped solvent (104) is pumped through a cooling soil (106) to solvent storage (174).

A bench scale operation of the described process as diagramed in FIG. 4 was fabricated in the laboratory to determine quantitative yields under optimized conditions. The nutrient mixture fed to the culture was as follows:

1. 80.0 ml of a salt, composed of:

| | |
|---|---|
| $KH_2PO_4$ | 3.00 g/L |
| $K_2HPO_4$ | 3.00 g/L |
| $(NH_4)_2SO_4$, | 6.00 g/L |
| NaCl | 6.00 g/L |
| $MgSO_4.2H_2O$ | 1.25 g/L |

2. 1.0 g of yeast extract
3. 1.0 g of trypticase
4. 3.0 ml of PFN trace metal solution (Pfenning] containing:

| | |
|---|---|
| $FeCl_2 * 4H_2O$ | 1500 mg |
| $ZnSO_4 * 7H_2O$ | 100 mg |
| $MnCl_2 * 4H_2O$ | 30 mg |
| $H_3BO_3$ | 300 mg |
| $CoCl_2 * 6H_2O$ | 200 mg |
| $CuCl_2 * H_2O$ | 10 mg |
| $NiCl_2 * 6H_2O$ | 20 mg |
| $NaMoO_4 * 2H_2O$ | 30 mg |
| $Na_2SeO_3$ | 10 mg |
| Distilled water | 1000 ml |

5. 10.0 ml of B vitamins:

| | |
|---|---|
| Pyridoxal HCl | 10 mg |
| Riboflavin | 50 mg |
| Thiamine HCl | 50 mg |
| Nicotinic acid | 50 mg |
| Ca-D-Pantotheinate | 50 mg |
| Lipoic Acid | 60 mg |
| P-aminobenzoic acid | 50 mg |
| Folic acid | 20 mg |
| Biotin | 20 mg |
| Cyanocobalamin | 50 mg |
| Distilled water | 1000 ml |

6. 0.5 g of Cysteine HCl
7. 0.6 g of $CaCl_2.2H_2O$
8. 2.0 g of $NaHCO_3$
9. 1.0 ml of Resazurin (0.01%)
10. 920.0 ml of distilled water For use with *A. kivui*, the nutrient solution was pH adjusted to 6.6, whereas for the new strain, *C. ljungdahlii* ERI2, the pH was adjusted to 4.9. The ability to operate at a lower pH is a great advantage in acetic acid recovery. The solution was then sparged for 20 minutes with a 20% $CO_2$ and 80% $N_2$ atmosphere, then transferred anaerobically and autoclaved for 15 minutes.

B. CSTR Experiments Utilizing the Bacterial Strains *A. kivui* and *C. ljungdahlii* ERI2

Numerous experiments were carried out with Continuous Stirred Reactors (CSTR). The results obtained are exemplified in the following data. The bench scale system operating with the CSTR and the anaerobic bacteria, *C. ljungdahlii* ERI2 and *A. kivui*, consisted of a New Brunswick Scientific Bioflo IIc fermenter, a hollow fiber membrane unit for cell recycle, and extraction and distillation columns. Nutrient mixture was fed into the bioreactor at a rate of 3.2 cubic centimeters per minute. Capacity of the reactor was 2.5 liters, within which a constant fluid level of 1.5 liters was maintained. The fluid was agitated at variable rates of up to 1000 revolutions per minute with gas introduced at a rate of approximately 500 cubic centimeters per minute. Optimal gas retention times were in the range of three minutes. The gas feed varied with its uptake by the bacteria, which was in turn a function of the cell density. The liquid from the bioreactor was passed to the hollow fiber membrane at a rate of 55 to 70 milliliters per minute. From the hollow fiber membrane, permeate was gathered at a rate of 1.5 milliliters per minute.

Analysis of this permeate indicates the acetic acid/acetate concentration at this stage to range in excess of 20 grams per liter. Operating at a pH of 4.9, 42 percent of this product was in the acid form using *C. ljungdahlii* ERI2. For *A. kivui*, the acid yield was only 1.4 percent. Results of various runs for the two bacteria, including conversion rates and product yields are summarized in Tables 2A, 2B, 3A and 3B as follows:

TABLE 2A

Summary of ERI2 Experiments in the CSTR with Cell Recycle

| Exp No. | Gas Retention Time (min) | Liquid Dilution Rate ($hr^{-1}$) | Agitation Rate (rpm) | Percent Gas Conversion CO | $H_2$ |
|---|---|---|---|---|---|
| 1 | 9.30 | 0.056 | 750 | 80.75 | 74.5 |
| 2 | 9.28 | 0.055 | 750 | 82.1 | 72.0 |
| 3 | 6.14 | 0.061 | 750 | 73.6 | 46.5 |
| 4 | 6.4 | 0.08 | 750 | 74.8 | 49.6 |
| 5 | 4.74 | 0.087 | 750 | 68.5 | 37.2 |
| 6 | 4.91 | 0.10 | 750 | 68.8 | 50.2 |
| 7 | 4.05 | 0.102 | 750 | 65.5 | 58.1 |
| 8 | 3.98 | 0.103 | 900 | 74.3 | 67.9 |
| 9 | 2.89 | 0.117 | 900 | 66.1 | 33.9 |
| 10 | 3.28 | 0.105 | 1000 | 74.6 | 51.3 |
| 11 | 3.22 | 0.125 | 1000 | 73.1 | 54.0 |
| 12 | 2.63 | 0.13 | 1000 | 68.9 | 44.0 |
| 13 | 2.3 | 0.134 | 1000 | 66.0 | 38.7 |
| 14 | 2.7 | 0.11 | 1000 | 72.7 | 67.7 |
| 15 | 2.4 | 0.11 | 1000 | 68.6 | 63.3 |
| 16 | 2.53 | 0.122 | 1000 | 72.1 | 67.4 |
| 17 | 3.0 | 0.13 | 1000 | 76.6 | 73.3 |

TABLE 2B

Summary of ERI2 Experiments in the CSTR with Cell Recycle

| Exp. No. | Dry Cell Weight Concentration (g/L) | Product Concentration HAC (g/L) | Product Concentration ETOH (g/L) | Specific Productivities (g/L hr) | Specific Productivities (g/g hr) |
|---|---|---|---|---|---|
| 1 | 2.3 | 9.7 | 0.07 | 0.43 | 0.18 |
| 2 | 3.32 | 9.56 | 0.094 | 0.52 | 0.16 |
| 3 | 4.11 | 12.78 | 0.125 | 0.78 | 0.19 |
| 4 | 5.02 | 12.98 | 0.125 | 1.05 | 0.19 |
| 5 | 4.79 | 12.38 | 0.125 | 1.08 | 0.23 |
| 6 | 4.53 | 10.73 | 0.05 | 1.08 | 0.24 |
| 7 | 5.27 | 11.49 | 0.076 | 1.17 | 0.22 |
| 8 | 6.17 | 12.73 | 0.1 | 1.31 | 0.21 |
| 9 | 5.91 | 11.69 | 0.04 | 1.38 | 0.23 |
| 10 | 7.30 | 12.83 | 0.13 | 1.35 | 0.18 |
| 11 | 10.25 | 13.57 | 0.08 | 1.71 | 0.17 |
| 12 | 11.0 | 14.63 | 0.12 | 1.90 | 0.17 |
| 13 | 11.1 | 20.59 | 0.113 | 2.77 | 0.25 |
| 14 | 8.37 | 25.62 | 0.27 | 2.88 | 0.34 |
| 15 | 9.83 | 25.62 | 0.36 | 2.95 | 0.30 |
| 16 | 9.82 | 25.62 | 0.72 | 3.12 | 0.32 |
| 17 | 12.4 | 22.33 | 0.52 | 2.90 | 0.23 |

TABLE 3A

Summary of A. kivui Experiments in the CSTR with Cell Recycle

| Exp No. | Gas Retention Time (min) | Liquid Dilution Rate (hr$^{-1}$) | Agitation Rate (rpm) | Percent Gas Conversion CO | Percent Gas Conversion H$_2$ |
|---|---|---|---|---|---|
| 1 | 5.0 | 0.058 | 750 | 67.8 | 44.2 |
| 2 | 4.4 | 0.958 | 750 | 65.7 | 38.5 |
| 3 | 4.3 | 0.058 | 900 | 71.3 | 40.7 |
| 4 | 3.72 | 0.058 | 900 | 69.0 | 37.3 |
| 5 | 3.72 | 0.076 | 900 | 70.3 | 41.1 |
| 6 | 3.2 | 0.076 | 900 | 66.4 | 41.4 |
| 7 | 2.8 | 0.076 | 900 | 61.5 | 29.1 |
| 8 | 2.8 | 0.076 | 1000 | 69.5 | 36.3 |
| 9 | 2.8 | 0.11 | 1000 | 70.2 | 41.6 |
| 10 | 2.2 | 0.11 | 1000 | 64.0 | 25.0 |

TABLE 3B

Summary of A. kivui Experiments in the CSTR with Cell Recycle

| Exp. No. | Dry Cell Weight Concentration (g/L) | Product Concentration (g/L) | Specific Productivities (g/L hr) | Specific Productivities (g/g hr) |
|---|---|---|---|---|
| 1 | 4.00 | 16.15 | 0.96 | 0.24 |
| 2 | 4.8 | 16.63 | 0.94 | 0.19 |
| 3 | 4.5 | 17.03 | 0.99 | 0.21 |
| 4 | 5.14 | 19.16 | 1.13 | 0.22 |
| 5 | 5.28 | 16.17 | 1.21 | 0.23 |
| 6 | 5.71 | 16.85 | 1.23 | 0.23 |
| 7 | 5.00 | 16.16 | 1.22 | 0.23 |
| 8 | 5.8 | 18.58 | 1.62 | 0.29 |
| 9 | 5.9 | 18.4 | 1.84 | 0.36 |
| 10 | 7.2 | 16.5 | 2.1 | 0.3 |

C. ICR Experiments Utilizing the Bacterial Strain *C. ljungdahlii* ERI2

Numerous experiments were carried out with Immobilized Cell Reactors (ICR). The results obtained are exemplified in the following data. An ICR, consisting of a 2 inch outside diameter by 24 inch tall glass tube packed with fabric to support the cells and Enkamat 7020 immobilizing medium, was also tested in the acetic acid production process. With *C. ljungdahlii* ERI2 as the acetogenic anaerobe, 100 percent of the carbon monoxide and 79 percent of the hydrogen were converted at a gas retention time of 20 minutes. Acetic acid concentrations in the removed liquid were approximately 6.0 grams per liter. Results of the ICR studies are summarized in Table 4.

TABLE 4

Fabric ICR Performance with ERI2

| Liquid Dilution Rate (hr) | Gas Retention Time (min) | H$_2$ Conversion (%) | CO Conversion (%) | Cell Concen. (g/L) | Product Concentration HAC (g/L) | Product Concentration ETOH (g/L) |
|---|---|---|---|---|---|---|
| 0.23 | 4.83 | 38.62 | 54.66 | .125 | 3.221 | .778 |
|  | 7.41 | 49.15 | 70.87 | .120 | 2.690 | .620 |
|  | 11.66 | 51.31 | 80.61 | .067 |  |  |
|  | 13.61 | 56.87 | 83.93 | .064 | 2.099 | .201 |
| 0.17 | 6.39 | 48.15 | 73.27 | .161 | 3.382 | 1.365 |
|  | 11.21 | 68.96 | 92.82 | .143 | 3.189 | .495 |
|  | 55.44 | 83.13 | 96.27 | .112 | .813 | .058 |
| 0.12 | 6.26 | 43.89 | 70.76 | .094 | 3.864 | 1.689 |
| 0.09 | 7.87 | 42.40 | 79.72 | .095 | 4.423 | 2.733 |
|  | 19.82 | 59.63 | 92.92 | .102 |  |  |
| 0.03 | 22.14 | 55.01 | 94.21 | .071 | 4.878 | 2.631 |
|  | 29.00 | 78.60 | 100 | .018 | 5.604 | 2.743 |
|  | 60.48 | 83.33 | 100 |  |  |  |

The ICR has a certain attractiveness on an industrial scale in that the energy costs to operate the reactor are reduced significantly. The proper selection of packing materials, solution phases, and pressures may yield production approaching that of the CSTR.

D. Acetic Acid Recovery

Various solvents were tested for recovering acetic acid from the permeate, and the results are summarized in Table 5. Tributyl phosphate was identified as having both a high distribution coefficient and a high boiling point. The solvent and permeate from the cell separator were commingled in a two stage extraction process. Alternatively, an extraction column could be used. Permeate was introduced into a 3 liter flask where it was mixed with incoming solvent. A ratio of 1 part solvent to 1 part permeate worked well and gave high recovery rates. The combined fluids were passed from the mixer to a 4 liter settling chamber where the solvent/acetic acid mixture separate as a lower density phase from the water and nutrients. Retention times of approximately 15 minutes were used in the settling tanks. The lower density phase was extracted and fed to a distillation flask.

The raffinate was passed from the first settler to a second mixer where it was contacted again with solvent, then removed to a second settling chamber. This allowed for more complete extraction of the acetic acid; acid recovery increased from 82 percent to greater than 96 percent using tributyl phosphate. The solvent/acetic acid mixture from this settler was returned to the first mixer, while the raffinate of water and organics was passed back to the bioreactor.

The distillation unit was a 5 liter flask with a boiling mantle. A common distillation column, with reflux, could be used for complete acid recovery. Because of the high boiling point of tributyl phosphate, nearly complete recovery is accomplished in one step. The solvent/acetic acid mixture was heated to 120° C., with the acetic acid collected overhead in a condensing coil. In this single stage system, distillation efficiencies of 70 percent were achieved.

TABLE 5

Acetic Acid Distribution Coefficient Study

| Solvent | Equilibrium Aqueous Acetic Acid Concentration (g/L) | Acetic Acid Distribution Coefficients |
|---|---|---|
| Hexane | 6.559 | 0.0 |
| Decane | 5.968 | 0.08 |
| Chloroform | 5.128 | 0.09 |
| Kerosene | 4.648 | 0.11 |
| Hexadecane | 5.866 | 1.13 |
| Dodecane | 4.654 | 0.13 |
| Dodecyl acetate | 5.787 | 0.15 |
| Dibutyl phosphate | 4.615 | 0.18 |
| Oleyl alcohol | 5.114 | 0.28 |
| Trioctylamine | 3.785 | 0.31 |
| Undecyl alcohol | 4.528 | 0.40 |
| Ethyl acetate | 4.550 | 0.41 |
| Ethyl butyrate | 4.665 | 0.42 |
| Dexyl alcohol | 3.890 | 0.42 |
| Octanol | 4.358 | 0.45 |
| Nonyl alcohol | 3.470 | 0.55 |
| 2-ethyl-1-hexanol | 3.308 | 0.77 |
| 3-methylcyclohexanol | 2.110 | 1.26 |
| Cyclohexanone | 2.702 | 1.66 |
| Tributyl Phosphate | 1.657 | 2.38 |

Solvent mixtures were also tried and distribution coefficients of mixed solvents are summarized in Table 6.

TABLE 6

Distribution Coefficients of Mixed Solvents

| Solvent Mix | Distribution Coefficients | Percent Increase |
|---|---|---|
| Oleyl Alcohol (10 cc) | 0.17 | |
| Oleyl Alcohol (10 cc) + Cyc (1 cc) | 0.31 | 72 |
| Oleyl Alcohol (10 cc) + TBP (1 cc) | 0.29 | 61 |
| Oleyl Alcohol (10 cc) + Cyc (2 cc) | 0.45 | 150 |
| Oleyl Alcohol (10 cc) + TBP (2 cc) | 0.42 | 133 |
| Oleyl Alcohol (10 cc) + Cyc (3 cc) | 0.36 | 100 |
| Oleyl Alcohol (10 cc) + TBP (3 cc) | 0.42 | 133 |
| Oleyl Alcohol (10 cc) + Cyc (4 cc) | 0.35 | 94 |
| Oleyl Alcohol (10 cc) + TBP (4 cc) | 0.40 | 122 |
| Oleyl Alcohol (10 cc) + Cyc (6 cc) | 0.52 | 188 |
| Oleyl Alcohol (10 cc) + TBP (6 cc) | 0.65 | 261 |
| Oleyl Alcohol (10 cc) + Cyc (7 cc) | 0.69 | 283 |
| Oleyl Alcohol (10 cc) + TBP (7 cc) | 0.74 | 311 |

EXAMPLE 2
Production of Acetic Acid from Carbon Black Waste Gases at Higher Pressures Mass transport in the cellular reactions can be further enhanced by operating the system at increased pressures. Simple batch experiments were carried out to test the dynamics of this system. It was found that reaction rates increased in linear proportion to the pressure, with a corresponding reduction in effective retention time.

Figure 5:
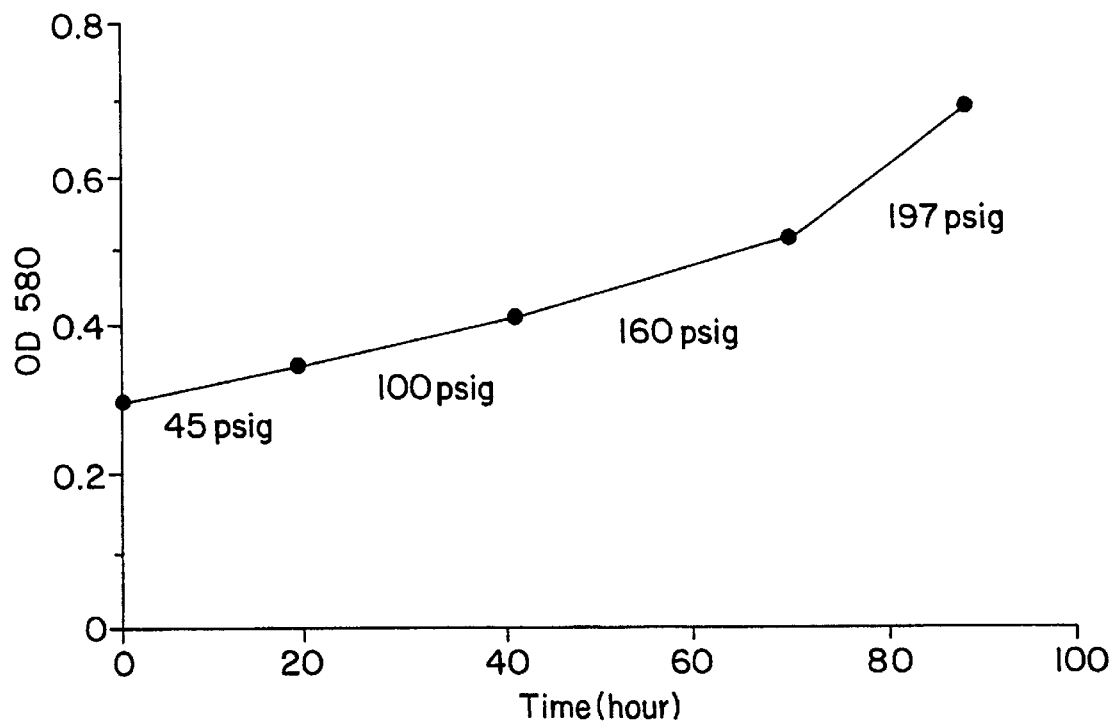
FIG. 5 is a graphical illustration of the increase in cell concentration measured in optical density at 580 nm (OD580) over time according to a method of this invention.
Figure 6:
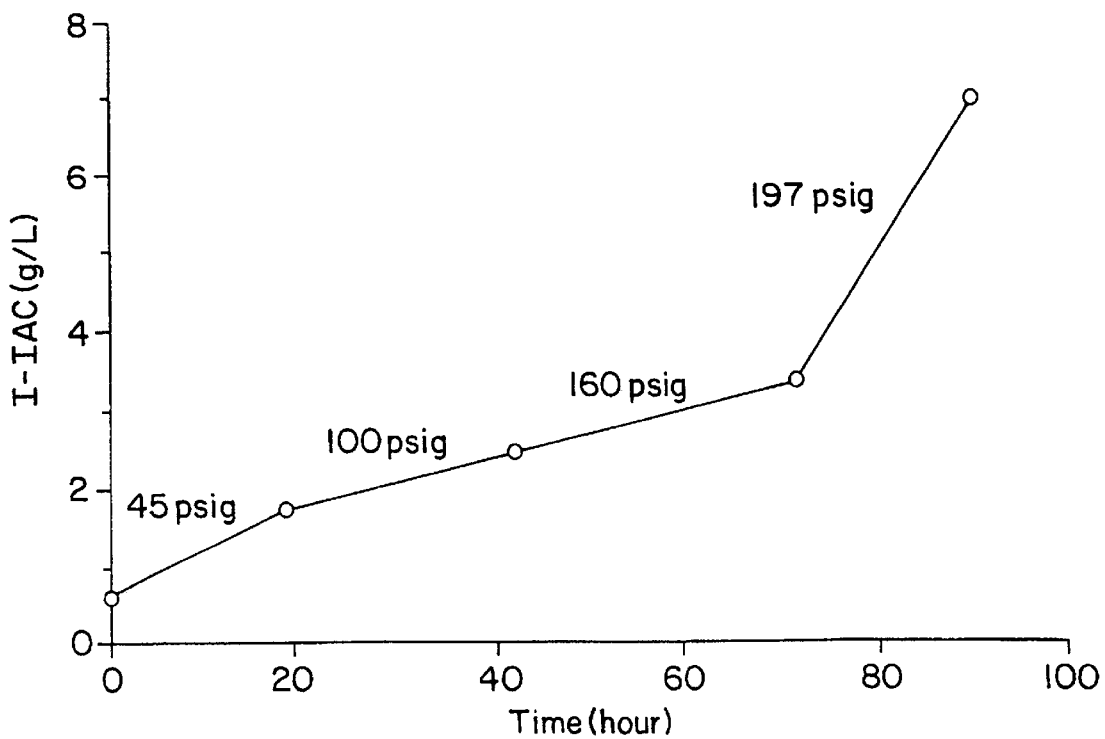
FIG. 6 is a graphical representation of an increase in acetic acid (IAC) produced by a method of this invention over time.

Another advantage to operating at increased pressure is that reactor volume can also be reduced in linear fashion, i.e. operation at 10 atmospheres pressure requires a reactor with one tenth the volume of a reactor operating at 1 atmosphere. FIGS. 5 and 6 show the increase in cell density and acetic acid concentration, respectively, with the increased pressure. This acetic acid concentration far exceeds typical batch concentrations for a batch reactor at atmospheric pressure.

EXAMPLE 3
Production of Acetic Acid from Carbon Black Waste Gases with Surfactants Mass transport is also increased by the use of surfactants. Table 7 presents the results of carbon monoxide uptake tests performed on *C. ljungdahlii* ERI2 in the presence of various commercial surfactants. In each case, the control value of 100 (percent) represents carbon dioxide uptake in batch fermentation, and the sample value, the percentage of the control in batch fermentation in the presence of the surfactant.

TABLE 7

CO Consumption by ERI2 in the Presence of Surfactants

| | Control* | With Surfactant |
|---|---|---|
| DNAP (0.1%, v/v) | 100 | 0 |
| Nondiet P-40 (0.1%, v/v) | 100 | 0 |
| Tergitol NP-10 (0.1%, v/v) | 100 | 0 |
| Tergitol Min Foam 1X (0.1%, v/v) | 100 | 0 |
| Tergitol TMN-10 (0.1%, v/v) | 100 | 0 |
| Triton X-15 (0.1%, v/v) | 100 | 0 |
| Triton X-100 (0.1%, v/v) | 100 | 0 |
| Triton X-114 (0.1%, v/v) | 100 | 0 |
| Triton N-101 (0.1%, v/v) | 100 | 5.83 |
| Triton X-405 (0.1%, v/v) | 100 | 7.82 |
| Tergitol 8 (0.1%, v/v) | 100 | 12.15 |
| Triton N-42 (0.1%, v/v) | 100 | 42.90 |
| Witconol NS-500K (0.1%, v/v) | 100 | 79.08 |
| Tween 85 (0.1%, v/v) | 100 | 82.16 |
| Witconol H-33 (0.1%, v/v) | 100 | 90.12 |
| Witconol 6903 (0.1%, v/v) | 100 | 92.39 |
| Tween 80 (0.1%, v/v) | 100 | 97.15 |
| Arlacel 83 (0.1%, v/v) | 100 | 97.43 |
| Span 80 (0.1%, v/v) | 100 | 99.12 |
| Tyloxapol (0.1%, v/v) | 100 | 104.86 |
| Witconol 5906 (0.1%, v/v) | 100 | 108.42 |
| Span 85 (0.1%, v/v) | 100 | 124.85 |
| W-1 (0.001%, w/v) First time | 100 | 105.89 |
| Second time regas | 100 | 0 |
| Brij 96 (0.004%, w/v) First time | 100 | 107.98 |
| Second time regas | 100 | 0 |

EXAMPLE 4
Production of CMA from Carbon Black Waste Gas

Carbon black waste gas containing about 14 percent CO, 17 percent $H_2$, and 4 percent $CO_2$, as the major components in $N_2$ is spared into a 160 L CSTR, maintained at 6 atm 37° C., and containing *Clostridium ljungdahlii* ER12 ATCC deposit 55380. The waste gases are produced as the result of partial oxidation of hydrocarbons with insufficient air to form amorphous carbon, with about 1.2 pounds of carbon monoxide produced per pound of elemental carbon. These waste gases form a serious atmospheric contamination problem and also represent a valuable chemical feedstock resource not presently being recovered. The gas retention time (defined as the ratio of the reactor volume to the gas flow rate at standard conditions) is maintained at 0.52 minute.

An aqueous liquid medium containing water, base salts, B-vitamins, a nitrogen source and a sulfide source is fed to the reactor at a liquid dilution rate (defined as the ratio of the liquid flow rate to the reactor volume) of 1.05 $hour^{-1}$. The agitation rate in this reactor is 322 rpm, the temperature is 37° C. and the operating pH is 5.03. Under these conditions, the conversion of CO was 83 percent and the conversion of $H_2$ was 54 percent. A hollow fiber membrane cell recycle unit is used to maintain a cell concentration of 10.5 g/L inside the reactor.

The dilute acetic acid/acetate product stream from the reactor containing 13.2 g/L acetic acid/acetate is sent to a three stage countercurrent extraction device, where it is extracted with solvent. The solvent to feed ratio is 1 to 4. The acetic acid in the acetic acid/acetate product stream is 3.7 g/L. The acetic acid concentration in the solvent leaving the extractor is 16.7 g/L. Water (medium) from extraction is sent back to the fermenter as recycle.

Dolomitic lime/MgO is added to the acetic acid directly in the solvent phase to form CMA. After reaction the saturated CMA solution is sent to drying and pelletizing. CMA (1.15 lb) containing a $Ca^{2+}/Mg^{2+}$ in a molar ratio of 3/7 is formed per pound of acetic acid.

EXAMPLE 5

Production of Acetic Acid from Carbon Black Waste Gas

Carbon black waste gas containing about 14 percent CO, 17 percent $H_2$, and 4 percent $CO_2$ in $N_2$ is spared into a 144 L trickle bed reactor operating at 1.58 atm, 37° C. and containing *Clostridium ljungdahlii* ER12 ATCC deposit 55380. A trickle bed reactor is a column packed with a commercial packing such as Raschig rings or Berl saddles in which liquid and gas are contacted with each other due to flow through the column. In the present example, the liquid and gas both enter the column from the top in a concurrent fashion, although countercurrent flow (gas entering the bottom, liquid entering the top) is possible. The gas retention time is maintained at 0.46 minute and the liquid medium dilution rate is 0.57 $hour^{-1}$. The liquid medium contains the same constituents as in Example 1. Agitation in the reactor is provided by liquid recirculation, using a recirculation rate of 60 gpm. The operating pH in the reactor is 5.05. Under these conditions, the CO conversion is 57 percent and the $H_2$ conversion is 58 percent. A hollow fiber unit is used to maintain a cell concentration of 13.6 g/L inside the reactor.

The dilute acetic acid/acetate product stream containing 6.4 g/L combined acetic acid/acetate and 2 g/L acetic acid is sent to a three stage countercurrent extraction column. The solvent to feed ratio is 1:4. The acetic acid in the solvent leaving the extractor is 10 g/L. Water (medium) from the extraction unit is sent back as recycle to the reactor.

The solvent containing the acetic acid is sent to distillation to recover the acid and solvent. A vacuum solvent distillation column and an acetic acid distillation column are used in the separation. Glacial acetic acid is produced as the final product.

EXAMPLE 6

Production of Potassium Acetate from Carbon Black Waste Gas

The carbon black waste gas of Example 4 is used to make potassium acetate instead of CMA. All fermentation and solvent extraction conditions remain the same. Caustic potash (potassium oxide) is used to react with the acetic acid to form a 50 percent solution of potassium acetate directly in the solvent phase.

EXAMPLE 7

Production SCP from Coke Oven Waste Gas

A coke oven waste gas containing about 6 percent CO, 2 percent $CO_2$, 57 percent $H_2$, 5 percent $N_2$, and 27 percent gaseous hydrocarbon is fed to a CSTR with cell recycle as described previously in Example 4. The reactor is used to produce a product such as dilute acetic acid or ethanol. In addition, the cell concentration inside the reactor is 13.6 g/L. These cells (microorganisms) can be harvested to produce bacterial single cell protein as an animal feed. A purge stream from the reactor containing cells is sent to a dryer to process dry single cell protein.

EXAMPLE 8

Production of $H_2$ from Refinery Waste Gas

Refinery waste gas containing about 45 percent CO, 50 percent $H_2$ and 5 percent $CH_4$ is spared into a 1 L CSTR operating at 50° C. and a few inches of water pressure containing *Bacillus smithii* ERIH2 which was deposited on Mar. 18, 1993 with the American Type Culture Collection, and given deposit accession no. 55404. This deposit was released to the public on Oct. 13, 1998. The medium to the reactor is 1.0 g/L corn steep liquor. Carbon monoxide in the waste gas is converted along with water to $CO_2$ and $H_2$. With a 90 percent conversion, the exit gas stream contains 3.2 percent CO, 64.4 percent $H_2$, 28.8 percent $CO_2$ and 3.6 percent $CH_4$. The CO, $CO_2$ and $CH_4$ are removed from the gas stream by solvent extraction.

EXAMPLE 9

Production of Other Chemicals from Carbon Black Waste Gas

Carbon black waste gas containing about 14 percent CO, 17 percent $H_2$ and 4 percent $CH_4$ in $N_2$ is spared into a 1 L CSTR operating at 37° C. and a few inches of water pressure. The medium in the reactor is a basal salts mixture containing water, B-vitamins, salts and minerals. The single or mixed culture in the reactor produces a liquid phase product of methanol, propanol, buytanol, propionic acid, butyric acid or other desirable products. The system is set up essentially the same as in Example 8.

Following dilute product formation, the product is recovered in a suitable product recovery system consisting of extraction, distillation or other well-known product recovery techniques. If multiple products are produced, a stagewise product recovery system is employed.

EXAMPLE 10

Production of Products from Waste Gas Using a Mixed Culture

The oil refinery waste gases of Example 8 are spared into a 1.0 L CSTR without cell recycle containing a mixed culture of bacteria capable of producing ethanol as the final product. The mixed culture contains one or more anaerobic bacteria that are capable of producing ethanol at low pH and under nutrient limitation. Other strains can also be present. The conditions inside the reactor are essentially identical to the conditions of Example 8. The product from the reactor is 15–20 g/L ethanol and 3–6 g/L acetic acid. The product stream from the reactor is treated identically to the method described in Example 8.

EXAMPLE 11
Production of Ethanol from Waste Gas Using *C. ljungdahlii* PETC

The oil refinery waste gases of Example 8 are spared into a 1.0 L CSTR without cell recycle containing a culture of *C. ljungdahlii* PETC capable of producing ethanol as the final product. The conditions inside the reactor are essentially identical to the conditions of Example 8. The product from the reactor is 15 g/L ethanol and 6 g/L acetic acid. The product stream from the reactor is treated identically to the method described in Example 8.

Thus, it will be appreciated that as a result of the present invention, a highly effective improved process for converting waste gases to acids, including organic acids, e.g., acetic acid, alcohols, hydrogen, SCP or organic acid salts is provided by which the principle objective, among others, is completely fulfilled. It is contemplated and will be apparent to those skilled in the art from the preceding description and accompanying drawings that modifications and/or changes may be made in the illustrated embodiments without departure from the present invention. Accordingly, it is expressly intended that the foregoing description and accompanying drawings are illustrative of preferred embodiments only, and are not limiting, and that the true spirit and scope of the present invention be determined by reference to the appended claims.

What is claimed is:

1. A process for producing acetic acid comprising the steps of:
   (a) providing a continuous flow of an oxygen-free gas substrate selected from the group consisting of:
      (i) a gas substrate comprising carbon monoxide,
      (ii) a gas substrate comprising carbon monoxide and hydrogen, and
      (iii) a gas substrate comprising hydrogen and carbon dioxide into a fermentation reactor;
   said fermentation reactor containing an aqueous nutrient medium and an anaerobic acetogenic *C. ljungdahlii* bacterium;
   (b) directing a continuous flow of said liquid nutrient medium into said fermentation reactor;
   (c) fermenting said nutrient medium, and said gas using said bacterium at a pH in said fermentation reactor of less than about 5.1;
   wherein at least 2 g/L of said acetic acid is produced in free acid form in said fermentation reactor in a broth;
   (d) continuously removing a portion of said broth containing acetic acid from said fermentation reactor; and
   (e) recovering the acetic acid therefrom by contacting said removed broth containing the product with a water-immiscible solvent having an affinity for said acetic acid and optionally distilling said acetic acid from said water-immiscible solvent.

2. The process according to claim 1 wherein said gas is generated by an industrial process selected from the group consisting of the manufacture of carbon black, ammonia, the production of methanol, the production of coke, and the refining of petroleum.

3. The process according to claim 1 wherein said fermentation reactor is selected from the group consisting of continuously stirred tank reactor, an immobilized microbial cell bioreactor, a trickle bed bioreactor, a bubble column bioreactor, and a gas lift bioreactor.

4. The process according to claim 1 wherein said fermentation reactor is maintained at a pressure of greater than one atmosphere.

5. The process according to claim 1 wherein said recovery step comprises separating said acetic acid and said bacterium by passing said removed broth containing acetic acid through a cell separation unit, returning said bacterium to the fermentation reactor to maintain a high bacterial concentration and producing a bacterium-free, acetic acid-containing stream.

6. The process according to claim 5 wherein said separating is accomplished by a step selected from the group consisting of centrifugation, hollow fiber membrane filtration, settling and ultrafiltration.

7. The process according to claim 1 wherein the process is conducted in the absence of cell separation from said broth.

8. The process according to claim 1 wherein said recovery of acetic acid is accomplished by (a) contacting said broth containing the acetic acid with a water-immiscible solvent having a high affinity for the acetic acid in a counterflow mixing vessel and then (b) optionally distillating the acetic acid of (a) to recover said water-immiscible solvent and acetic acid.

9. The process according to claim 1 wherein said recovery of acetic acid is accomplished by distillation.

10. The process according to claim 1 wherein said anaerobic acetogenic *Clostridium ljungdahlii* bacterium is PETC.

11. The process according to claim 1 wherein said anaerobic acetogenic *C. ljungdahlii* bacterium is *C. ljungdahlii* ERI-2.

12. The process according to claim 1 wherein said fermentation reactor further contains another anaerobic acetogenic bacterium selected from the group consisting of *Acetobacterium kivui*, *A. woodii*, *Butyribacterium methylotrophicum*, *Clostridium aceticum*, *C. acetobutylicium*, *C. formoacetium*, *C. kluyveri*, *C. thermoaceticum*, *C. thermocellum*, *C. thermohydrosulfuricum*, *C. thermosaccharolyticum*, *Eubacterium limosum*, *Peptostreptococcus productus*, *Rhodospiorillum rubrum* and *Rhodopseudomonas gelatinosa*.

13. The process according to claim 1 wherein said gas substrate (i) or (ii) further contains carbon dioxide.

14. The process according to claim 13, wherein said gas substrate further contains a component selected from the group consisting of nitrogen and methane.

15. The process according to claim 1, wherein the pH in the fermentation reactor is about 4.9.

16. The process according to claim 1 wherein said process was performed at greater than 15 atmospheres of pressure.

17. The process according to claim 1 wherein said fermentation reactor further contains a surfactant which increases the consumption of carbon monoxide by said bacterium.

18. The process according to claim 1 wherein said gas substrate further comprises one or more of nitrogen and methane.

19. The process according to claim 1, wherein after said recovery step, the acetic acid is contacted with dolomitic lime and magnesium oxide and dried, thereby producing calcium magnesium acetate.

20. The process according to claim 1, wherein after said recovery step, the acetic acid is contacted with caustic potash and dried, thereby producing potassium acetate.

* * * * *

UNITED STATES PATENT AND TRADEMARK OFFICE
CERTIFICATE OF CORRECTION

PATENT NO. : 6,340,581
DATED : January 22, 2002
INVENTOR(S) : James L. Gaddy

It is certified that error appears in the above-identified patent and that said Letters Patent is hereby corrected as shown below:

Title page,
Item [56] References Cited, replace "4,721,676" with -- 4,781,676 --.

Column 1,
Line 18, replace "07/220,686" with -- 08/220,686 --.

Column 3,
Line 50, replace "know" with -- known --.

Signed and Sealed this

Twenty-first Day of May, 2002

Attest:

Attesting Officer

JAMES E. ROGAN
Director of the United States Patent and Trademark Office

UNITED STATES PATENT AND TRADEMARK OFFICE
CERTIFICATE OF CORRECTION

PATENT NO. : 6,340,581 B1 Page 1 of 1
APPLICATION NO. : 09/219395
DATED : January 22, 2002
INVENTOR(S) : Gaddy It is certified that error appears in the above-identified patent and that said Letters Patent is hereby corrected as shown below:

Replace the following item (60) "Related U.S. Application Data" on the title page:

"Continuation-in-part of application No. 08/808,088, filed on Feb. 28, 1997, no Pat. No. 5,821,111, which is a continuation of application No. PCT/US96/11146, filed on Jul. 1, 1996, which is a continuation-in-part of application No. 08/674,417, filed on Jul. 1, 1996, now Pat. No. 5,136,577, which is a continuation-in-part of application No. 08/347,512, filed on Nov. 30, 1994, now Pat. No. 5,807,722, which is a continuation of application No. 08/258,446, filed on Jun. 10, 1994, now Pat. No. 5,593,886, which is a continuation of application No. 07/220,686, filed on Mar. 31, 1994, now abandoned, which is a division of application No. 07/968,857, filed on Oct. 30, 1992, now abandoned."

With the following "Related U.S. Application Data":

-- Continuation of application No. PCT/US96/11146, filed on Jul. 1, 1996, and

Continuation-in-part of application No. 08/674,417, filed on Jul. 1, 1996, now Pat. No. 5,136,577, which is a continuation-in-part of application No. 08/347,512, filed on Nov. 30, 1994, now Pat. No. 5,807,722, which is a continuation of application No. 08/258,446, filed on Jun. 10, 1994, now Pat. No. 5,593,886, which is a division of application No. 07/968,857, filed on Oct. 30, 1992, now abandoned, and Continuation-in-part of application No. 08/808,088, filed on Feb. 28, 1997, now Pat. No. 5,821,111, which is a continuation of application No. 08/220,686, filed on Mar. 31, 1994, now abandoned. --

Signed and Sealed this

Twenty-sixth Day of February, 2008

JON W. DUDAS
*Director of the United States Patent and Trademark Office*